(12) United States Patent
Myerson et al.

(10) Patent No.: US 7,435,810 B2
(45) Date of Patent: *Oct. 14, 2008

(54) USE OF IONIC LIQUIDS FOR FABRICATION OF POLYNUCLEOTIDE ARRAYS

(75) Inventors: Joel Myerson, Berkeley, CA (US); Michel G M Perbost, Bethany, CT (US); Douglas J Dellinger, Boulder, CO (US); Geraldine F Dellinger, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 589 days.

This patent is subject to a terminal disclaimer.

(21) Appl. No.: 11/020,428

(22) Filed: Dec. 22, 2004

(65) Prior Publication Data
US 2005/0112679 A1    May 26, 2005

Related U.S. Application Data

(63) Continuation of application No. 10/001,044, filed on Oct. 31, 2001, now Pat. No. 6,852,850.

(51) Int. Cl.
  C07H 21/00    (2006.01)
  C07H 21/02    (2006.01)
  C07H 21/04    (2006.01)
(52) U.S. Cl. ............... 536/25.3; 536/25.33; 536/25.34; 536/22.1; 536/23.1; 536/25.41
(58) Field of Classification Search .................. None
See application file for complete search history.

(56) References Cited

U.S. PATENT DOCUMENTS

| 6,022,963 | A | 2/2000 | McGall et al. | |
|---|---|---|---|---|
| 6,069,243 | A | 5/2000 | Scozzari | |
| 6,222,030 | B1 | 4/2001 | Dellinger et al. | |
| 6,242,266 | B1 | 6/2001 | Schleifer et al. | |
| 6,274,725 | B1 | 8/2001 | Sanghvi et al. | |
| 6,852,850 | B2 * | 2/2005 | Myerson et al. ............ | 536/25.3 |
| 6,858,720 | B2 * | 2/2005 | Myerson et al. ............ | 536/25.3 |

FOREIGN PATENT DOCUMENTS

| EP | 0742287 A2 | 9/1996 |
|---|---|---|
| WO | WO96/28457 | 9/1996 |
| WO | WO98/39348 | 3/1998 |
| WO | WO99/54509 | 4/1998 |
| WO | WO00/18778 | 9/1998 |
| WO | WO00/31594 | 4/2000 |

OTHER PUBLICATIONS

Serge L. Beaucage and Radhakrishnan P. Iyer, "Advances in the Synthesis of Oligonucleotides by the Phosphoramidite Approach"; Tetrahedron Report No. 309, Vo. 48, No. 12, pp. 2223-2313, 1992.

Ahmad Hasan, Hong Li, Jeno Toamsz and Barbara Ramsay Shaw; " Base-boronated Dinucleotides: synthesis and effect of N7-cyanoborane substitution on the base protons"; Nucleic Acids Research, 1996 vol. 24, No. 11; pp. 2150-2157.

Frank Bergman, Erich Kueng, Patrick Iaiza, and Willi Bannwarth; Allyl as Internucleotide Protecting Group in DNA Synthesis to be cleaved off by Ammonia; Tetrahedron, vol. 51, No. 25, 99. 6971-6976, 1995.

Frank Bergman and Wolfgang Pfleiderer; "Nucleotides"; The 2-Dansylethoxycarbonyl (=2-{[5-(Dimethylamino)napththalen-1-yl]sulfonyl} ethoxcarbonyl; Dnseoc) Group for Protection of the 5'-Hydroxy Function in Ologodeoxyribonucleotide Synethesis; Helvetica Chimica Acta—vol. 77(1994); pp. 203-213.

Michael C. Pirrung and Lora Fallon; Glenn McGall "Proofing of Photolithographic DNA Synthesis with 3', 5'—Dimethoxybenzoinyloxycarbonyl-Protected Doxynucleoside Phosphoramidites"; 1998 American Chemical Society, pp. 241-246.

Haraold Sigmund, Thomas Maier and Wolfgang Pfeiderer; A New Type of Fluorescence Labeling of Nucleosides Nucleotides and Oligonucleotides:; Nucleosides & Nucleotides, 16(5&6), pp. 685-696 (1997).

Glenn H. McGall, Anthony D. Barone, Martin Diggelman, Stephen P. A. Fodor, Erik Gentalen, and Nam Ngo; "The Efficiency of Light-Directed Synthesis of DNA Arrays on Glass Substrates"; Journal of the American Chemical Society, vol. 119, No. 22, Jun. 4, 1997, pp. 5081-5090.

Michael C. Pirrung and Jean Claude-Bradley; "Comparison of Methods for Photochemical Phosphoramidite-Based DNA Synthesis", J. Org. Chem. 1995, vol. 60, pp. 6270-6276.

Hayes Dougan, John B. Hobbs, Jeffrey I. Weitz and Donald M. Lyster; "Sunthesis and Raioiodination of a Stannyl Oligofeoxyribonucleotide"; Nucleic Acids Research, 1997, vol. 25, No. 14, pp. 2897-2901.

Shegenori Iwai and Eiko Ohtsuka; "t'-Levulinyl and 2-tetrahydrofuranyl protection for the synthesis of oligoribonucleotides by the Phosphoramidite approach"; Nucleic Acids Research, vol. 16, No. 20, 1988.

Earle et al., "Ionic Liquids, Green solvents for the future", Pure Applied Chemistry, vol. 72, No. 7, pp. 1391-1398, 2000.

Earle et al., Paradigm Confirmed: The First Ude of Ionic Liquids to Dramatically Influence the Outcome of Chemical Reactions Organic Letters, vol. 6, No. 5, pp. 707-710, 2004.

* cited by examiner

*Primary Examiner*—Shaojia Anna Jiang
*Assistant Examiner*—Traviss C McIntosh, III (57) ABSTRACT

A method of fabricating polynucleotide arrays includes dissolving a nucleotide monomer, oligonucleotide, or polynucleotide in a solvent containing ionic liquid and depositing the resulting solution on an array substrate. The method has particular application to fabrication of an addressable array of polynucleotides on a substrate that carries substrate bound moieties each with a hydroxyl group. The process may be repeated at specific locations on the array to elongate the polynucleotide deposited on the array.

28 Claims, 2 Drawing Sheets

USE OF IONIC LIQUIDS FOR FABRICATION OF POLYNUCLEOTIDE ARRAYS

CROSS-REFERENCE TO RELATED APPLICATION

This application claims priority to and is a continuation of U.S. application entitled, "Use of Ionic Liquids for Fabrication of Polynucleotide Arrays", Ser. No. 10/001,044, filed Oct. 31, 2001, now U.S. Pat. No. 6,852,850, which is entirely incorporated herein by reference. This application relates to a U.S. Patent Application entitled "Method of Synthesizing Polynucleotides Using Ionic Liquids," having Ser. No. 09/999,623, filed Oct. 31, 2001, now U.S. Pat. No. 6,858,720, which is entirely incorporated herein by reference.

DESCRIPTION

1. Field of the Invention

The invention relates generally to methods of forming arrays of polynucleotides on planar surfaces. The invention more specifically relates to depositing a composition that includes an ionic liquid and appropriate nucleotide monomers, oligonucleotides, or polynucleotides upon a planar surface to chemically bond the monomers, oligonucleotides, or polynucleotides to the planar surface.

2. Background of the Invention

Oligonucleotides or polynucleotides immobilized on planar substrates are increasingly useful as diagnostic or screening tools. Polynucleotide arrays include regions of usually different sequence oligonucleotides or polynucleotides arranged in a predetermined configuration on the substrate. These regions (sometimes referenced as "features") are positioned at respective locations ("addresses") on the substrate. The arrays, when exposed to a sample, will exhibit an observed binding pattern. This binding pattern can be detected upon interrogating the array. For example, all polynucleotide targets (e.g. DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Polynucleotide arrays can be fabricated by depositing previously obtained polynucleotides onto a substrate, or by in situ synthesis methods. Various chemical schemes have been described for the synthesis of polynucleotides. Typically these methods use a nucleoside reagent of the formula:

(I)

in which:

A represents H or an optionally protected hydroxyl group;

B is a purine or pyrimidine base whose exocyclic amine functional group is optionally protected;

one of M or Q is a conventional protecting group for the 3' or 5'-OH functional group (or, optionally, a conventional 3' or 5'-OH protecting group at the end of an intervening (and optionally protected) polynucleotide sequence, e.g. such that eq. (I) can represent a modified polynucleotide) while the other is:

(II)

where x may be 0 or 1, provided that:

a) when x=1:

R' represents H and R" represents a negatively charged oxygen atom; or

R' is an oxygen atom and R" represents either an oxygen atom or an oxygen atom carrying a protecting group; and b) when x=0, R' is an oxygen atom carrying a protecting group and R" is either a hydrogen or a di-substituted amine group.

When x is equal to 1, R' is an oxygen atom and R" is an oxygen atom, the method is in this case the so-called phosphodiester method; when R" is an oxygen atom carrying a protecting group, the method is in this case the so-called phosphotriester method.

When x is equal to 1, R' is a hydrogen atom and R" is a negatively charged oxygen atom, the method is known as the H-phosphonate method.

When x is equal to 0, R' is an oxygen atom carrying a protecting group and R" is a halogen, the method is known as the phosphite method, and when R" is a leaving group of the disubstituted amine type, the method is known as the phosphoramidite method.

The conventional sequence used to prepare an oligonucleotide using reagents of the type of formula (I), basically follows four separate steps: (a) coupling a selected nucleoside which also has a protected hydroxy group, through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The in situ method for fabricating a polynucleotide array typically follows, at each of the multiple different addresses at which features are to be formed, the same conventional iterative sequence used in forming polynucleotides on a support by means of known chemistry. During array fabrication, different monomers may be deposited at different addresses on the substrate during any one iteration so that the different features of the completed array will have different desired polynucleotide sequences. The coupling can be performed by depositing drops of an activator and phosphoramidite at the specific desired feature locations for the array. One or more intermediate further steps may be required in each iteration, such as the conventional oxidation and washing steps.

Methods of depositing materials onto a planar substrate include loading and then touching a pin or capillary to a surface, such as described in U.S. Pat. No. 5,807,522, or deposition by firing from a pulse jet such as an inkjet head, such as described in PCT publications WO 95/25116 and WO 98/41531 and in U.S. Pat. No. 6,180,351, and elsewhere. For in situ fabrication methods, multiple different reagent droplets are deposited by pulse jet or other means at a given target location in order to form the final feature (hence a probe of the feature is synthesized on the array substrate). Some protocols flood the substrate with reagent solutions during one or more steps of the cycle, e.g. deprotection, oxidation, or washing steps.

The foregoing methods of preparing polynucleotides are well known and described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives, CRC Press, Boca Raton, Fla., pages 100 et seq., U.S. Pat. No. 4,415,732, U.S. Pat. No. 4,458,066, U.S. Pat. No. 4,500,707, U.S. Pat. No. 5,153,319, U.S. Pat. No. 5,869,643, EP 0294196, and elsewhere. The phosphoramidite and phosphite triester approaches are most broadly used, but other approaches include the phosphodiester approach, the phosphotriester approach and the H-phosphonate approach. Such approaches are described in Beaucage et al., Tetrahedron (1992) 12:2223-2311. A more recent approach for synthesis of polynucleotides is described in U.S. Pat. No. 6,222,030 B1 to Dellinger et al., issued Apr. 24, 2001.

Figure 1:
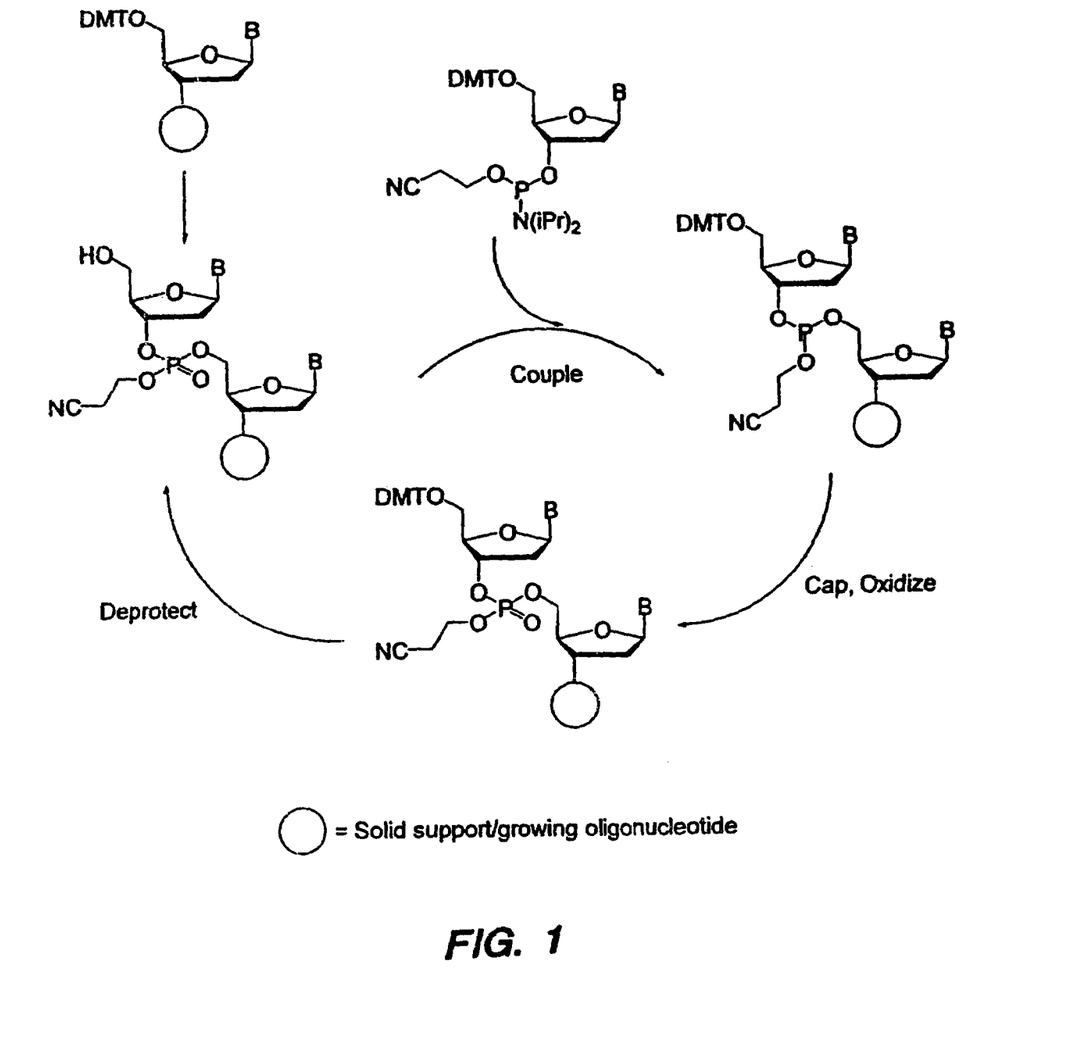

In the typical phosphoramidite method of solid phase oligonucleotide synthesis, the synthesis typically proceeds in the 3' to 5' direction (referring to the sugar component of the added nucleoside), although the synthesis may easily be conducted in the reverse direction. The added nucleoside generally has a dimethoxytrityl protecting group on its 5' hydroxyl and a phosphoramidite functionality on its 3' hydroxyl position. Beaucage et al. (1981) Tetrahedron Lett. 22:1859. See FIG. 1 for a schematic representation of this technology. In FIG. 1 "B" represents a purine or pyrimidine base, "DMT" represents dimethoxytrityl protecting group and "iPr" represents isopropyl. In the first step of the synthesis cycle, the "coupling" step, the 5' end of the growing chain is coupled with the 3' phosphoramidite of the incoming monomer to form a phosphite triester intermediate (the 5' hydroxyl protecting group prevents more than one monomer per synthesis cycle from attaching to the growing chain). Matteucci et al. (1981) J. Am. Chem. Soc. 103:3185. Next, the optional "capping reaction" is used to stop the synthesis on any chains having an unreacted 5' hydroxyl, which would be one nucleotide short at the end of synthesis. The phosphite triester intermediate is subjected to oxidation (the "oxidation" step) after each coupling reaction to yield a more stable phosphotriester intermediate. Without oxidation, the unstable phosphite triester linkage would cleave under the acidic conditions of subsequent synthesis steps. Letsinger et al. (1976) J. Am. Chem. Soc. 98:3655. Removal of the 5' protecting group of the newly added monomer (the "deprotection" step) is typically accomplished by reaction with acidic solution to yield a free 5' hydroxyl group, which can be coupled to the next protected nucleoside phosphoramidite. This process is repeated for each monomer added until the desired sequence is synthesized. A final deprotection step is provided in which nitrogenous bases and phosphate group are simultaneously deprotected by treatment with ammonium hydroxide and/or methylamine under known conditions.

According to some protocols, the synthesis cycle of couple, cap, oxidize, and deprotect is shortened by omitting the capping step or by taking the oxidation step 'outside' of the cycle and performing a single oxidation reaction on the completed chain. For example, oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

Conventional synthesis protocols of oligonucleotides are not without disadvantages. For example, cleavage of the DMT protecting group under acidic conditions gives rise to the resonance-stabilized and long-lived bis(p-anisyl)phenylmethyl carbocation. Gilham et al. (1959) J. Am. Chem. Soc. 81:4647. Protection and deprotection of hydroxyl groups with DMT are thus readily reversible reactions, resulting in side reactions during oligonucleotide synthesis and a lower yield than might otherwise be obtained. To circumvent such problems, large excesses of acid are used with DMT to achieve quantitative deprotection. The excess acid leads to the acid-catalyzed depurination of the oligonucleotides, thus impairing the synthesis. Caruthers et al., in Genetic Engineering: Principles and Methods, J. K. Setlow et al., Eds. (New York: Plenum Press, 1982).

Applications in the field of genomics and high throughput screening have fueled the demand for increased performance of analytical systems that use polynucleotide arrays. Thus, the arrays need to be fabricated with very small, densely packed features, increasing the need for very precise chemistry in such a context. Smearing or streaking of features becomes more problematice at small scales, as does undesirable hydrolysis of reagents. In particular, the reagents used in the coupling step typically are highly susceptible to hydrolysis. As feature size becomes smaller, the efficiency of the coupling reaction goes down because of increasing hydrolysis. The use of dry solvents and dry atmosphere for the synthesis has resulted in limited success at a greater cost.

The problems associated with the use of DMT are exacerbated in polynucleotide array synthesis where "microscale" parallel reactions are taking place on a very dense, packed surface. Thus, increasingly stringent demands are placed on the chemical synthesis cycle as it was originally conceived, and the problems associated with conventional methods for synthesizing oligonucleotides are rising to unacceptable levels in these expanded applications.

Salts that are fluid at room temperature have been investigated as environmentally friendly solvents. These salts have been termed 'room temperature ionic liquids' (herein simply referred to as 'ionic liquids') and are generally composed of a heterocyclic cation, e.g. a substituted imidazole or pyridine, and an anion such as tetrafluoroborate or hexafluorophosphate, although certain organic anions such as methylsulfate ($CH_3SO_4^-$), among others, have been discovered to be effective as the anion in certain organic liquids. Ionic liquids are known to dissolve a wide range of substances, both organic and inorganic. Ionic liquids typically are non-corrosive, have little or no vapor pressure under standard conditions, and exhibit low viscosity. More information regarding ionic liquids may be gleaned from two review articles by Hussey (Hussey, C. L., Adv. Molten Salt Chem. (1983) 5:185; and Hussey, C. L., Pure Appl. Chem. (1988) 60:1763).

SUMMARY OF THE INVENTION

The invention is thus addressed to the aforementioned deficiencies in the art, and provides novel methods for fabricating polynucleotide arrays, wherein the methods have numerous advantages relative to prior methods such as those discussed above. The methods involve a process of immobilizing a nucleotide monomer, oligonucleotide, or polynucleotide upon an insoluble substrate in the presence of an ionic liquid. The present invention provides a method of generating an addressable array of polynucleotides on a substrate. This method includes dissolving a nucleotide monomer, oligonucleotide, or polynucleotide in a solvent comprising an ionic liquid. An array substrate is then contacted with the resulting solution. The substrate has a surface reactive group which, when contacted with the resulting solution, reacts to covalently bind the nucleotide monomer, oligonucleotide, or polynucleotide to the substrate.

The invention encompasses a method for the formation of a bond between (a) a nucleotide monomer, olignucleotide or polynucleotide dissolved in a solvent comprising an ionic liquid, and (b) a reactive group on a substrate, where the reactive group may be a part of an immobilized nucleotide monomer, an immobilized oligonucleotide, or an immobilized polynucleotide, or the reactive group may be a part of the planar substrate base material or a surface modification of the base material. The formation of the bond thus results in the dissolved nucleotide monomer, olignucleotide or polynucleotide being immobilized to the planar substrate surface via the bond and via any immobilized oligonucleotide or polynucleotide previously immobilized on the surface.

The compositions and methods described are particularly useful for fabricating an addressable polynucleotide array by in situ synthesis of polynucleotides on the array substrate. In one such embodiment, at each of the multiple different addresses on the substrate (for example, at least one hundred, at least one thousand, or at least ten thousand addresses), the in situ synthesis cycle is repeated so as to form the addressable array with different polynucleotide sequences at different addresses. In the array forming method, the nucleosides to be coupled at respective addresses are dissolved in a solvent containing ionic liquid and deposited as droplets at those addresses.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates a prior art oligonucleotide synthesis method using phosphoramidite monomers. The known prior art methods, including the one illustrated, do not describe the use of ionic liquids in the coupling step where the internucleotide bond is formed.

To facilitate understanding, identical reference numerals have been used, where practical, to designate corresponding elements that are common to the Figures. Figure components are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. In this specification and in the claims that follow, reference will be made to a number of terms that shall be defined to have the following meanings unless a contrary intention is apparent:

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base. A "nucleoside moiety" refers to a molecule having a sugar group and a nitrogen containing base (as in a nucleoside) as a portion of a larger molecule, such as in a polynucleotide, oligonucleotide, or nucleoside phosphoramidite. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected. An "oligonucleotide" generally refers to a nucleotide multimer of about 2 to 100 nucleotides in length, while a "polynucleotide" includes a nucleotide multimer having any number of nucleotides. It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phospho or phosphite group, and may include linkages where one or more oxygen atoms of the phospho or phosphite group are either modified with a substituent or replaced with another atom, e.g. a sulfur atom, or the nitrogen atom of a mono- or di-alkyl amino group.

An "array", unless a contrary intention appears, includes any one, two or three dimensional arrangement of addressable regions bearing a particular chemical moiety or moieties (for example, polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). While probes and targets of the present invention will typically be single-stranded, this is not essential. An "array layout" refers to one or more characteristics of the array, such as feature positioning, feature size, and some indication of a moiety at a given location. "Hybridizing" and "binding", with respect to polynucleotides, are used interchangeably.

A "group" includes both substituted and unsubstituted forms. Typical substituents include one or more lower alkyl, any halogen, hydroxy, or aryl, or optionally substituted on one or more available carbon atoms with a nonhydrocarbyl substituent such as cyano, nitro, halogen, hydroxyl, or the like. Any substituents are typically chosen so as not to substantially adversely affect reaction yield (for example, not lower it by more than 20% (or 10%, or 5% or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

A "protecting group" is used in the conventional chemical sense to reference a group which reversibly renders unreactive a functional group under specified conditions of a desired reaction. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. A "hydroxyl protecting group" refers to a protecting group where the protected group is a hydroxyl. A "reactive-site hydroxyl" is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions. Preferred protecting groups that are capable of removal under acidic conditions ("acid-labile protecting groups") include those such as tetrahydropyranyl groups, e.g. tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. A trityl group is a triphenylmethyl group. Suitable protecting groups are described in "Protective Groups in Organic Synthesis" by T. W. Green, Wiley Interscience.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to eight carbon atoms, and includes, for example, methyl, ethyl, ni-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "alkenyl" as used herein, unless otherwise specified, refers to a branched, unbranched or cyclic (in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

The synthesis of polynucleotides has been well-studied, and methods incorporate both aqueous and organic solvents. It is well known that changing the solvent in a reaction system frequently affects the performance of the reaction, sometimes profoundly. The ionic nature of ionic liquids fundamentally differs from molecular nature of aqueous or organic solvents used in various steps of the polynucleotide synthesis cycle. Potential problems include changes of chemical mechanism, possibly favoring different products due to the ionic nature of the solvent. Stabilization of charged reaction intermediates due to interaction with the ionic liquid, or chemical reaction with components of the ionic liquid itself might be expected. Will the short-lived reaction intermediates found in conventional solvents be long-lived stable intermediates in an ionic liquid? Will changes in the relative stabilities of reaction intermediates change the available reaction pathways? Will the expected changes in reaction kinetics shift the balance between thermodynamic and kinetic control, and hence produce different products?

We determined to study the effect of the coupling reaction in ionic liquid solvent as an alternative to molecular solvents (aqueous and organic solvents). We have discovered that, despite the previously mentioned potential problems, we were able to achieve coupling of nucleoside moieties via formation of an internucleotide bond in ionic liquids. We have now found that various advantages exist in performing the coupling reaction in ionic liquids. One advantage we found was that the hydrophobicity of ionic liquid led to reduced problems in dealing with hydrolysis of the reactants due to water in the reaction environment. Less solvent may be used to wash in between coupling steps, and ionic liquid solvents may be recovered more easily, when compared to prior art methods. This may be particularly useful in large-scale synthesis, where lots of washing and solvents are required.

Particularly useful phosphoramidites, their preparation, and their use are described in detail in U.S. Pat. No. 5,902,878; U.S. Pat. No. 5,700,919; U.S. Pat. No. 4,668,777; U.S. Pat. No. 4,415,732; PCT publication WO 98/41531 and the references cited therein, among others.

The chemical synthesis of thymidine-thymidylate dimers in ionic liquid were preformed by the following protocol:

3 molecular sieves were activated by drying in a vacuum oven at 200° C. overnight. A small number of sieves were placed in a 5 ml, round bottom flask with a 14/20 ground glass joint that was then sealed with a rubber septum. 3 ml of 1-ethyl-3-methyl-1H-imidazolium trifluoromethane-sulfonate (Aldrich Chemical Company, Milwaukee, Wis. USA) was added to the flask and the liquid allowed to dry overnight. 5'-Dimethoxytrityl-2'-deoxyThymidine, 3'-[(2-cyanoethyl)-(N,N-diisopropyl)]-phosphoramidite, 0.38 grams, 0.5 mmol, was added to the flask and the solution shaken until the reagent had dissolved. A small amount of the solution was removed from the flask and placed in an NMR tube for analysis by $^{31}$P NMR using an external lock. The resulting NMR spectrum showed the presence of the starting material nucleoside phosphoramidite at δ 147.18 ppm relative to phosphoric acid.

3'-Acetyl Thymidine (ChemGenes Corp., Waltham Mass. USA) 0.14 grams, 0.5 mmol was added to the mixture along with tetrazole 0.18 grams, 2.5 mmol. The solution was shaken on a wrist action shaker until the reagents were completely dissolved. An aliquot of the reaction mixture was removed from the flask and placed in an NMR tube for analysis by $^-$P NMR using an external lock. The resulting NMR spectrum (FIG. 2) showed complete conversion of the starting material nucleoside phosphoramidite at δ 147.18 ppm to the phosphite triester at δ 139.16 ppm.

In another example, 3' molecular sieves were activated by drying in a vacuum oven at 200° C. overnight. A small number of sieves were placed in a 5 ml, round bottom flask with a 14/20 ground glass joint that was then sealed with a rubber septum. 3 ml of 1-butyl-3-methyl-imidazolium tetrafluoroborate (Solvent Innovation GmbH, 50679 Köln, Germany) was added to the flask and the liquid allowed to dry overnight. 5'-Dimethoxytrityl-2'-deoxyThymidine, 3'-[(2-cyanoethyl)-(N,N-diisopropyl)]-phosphoramidite, 0.38 grams, 0.5 mmol, was added to the flask and the solution shaken until the reagent had dissolved. A small amount of the solution was removed from the flask and placed in an NMR tube for analysis by $^-$P NMR using an external lock. The resulting NMR spectrum (FIG. 3) showed the presence of the starting material nucleoside phosphoramidite at δ 146.94 ppm relative to phosphoric acid.

3'-Acetyl Thymidine (ChemGenes Corp., Waltham Mass.) 0.14 grams, 0.5 mmol was added to the mixture along with tetrazole 0.18 grams, 2.5 mmol. The solution was shaken on a wrist action shaker until the reagents were completely dissolved. An aliquot of the reaction mixture was removed from the flask and placed in an NMR tube for analysis by $^{31}$P NMR using an external lock. The resulting NMR spectrum (FIG. 4) showed complete conversion of the starting material nucleoside phosphoramidite at δ 146.94 ppm to the phosphite triester diastereomers centered at δ 138.98 ppm.

The method of the above-described synthesis in the presence of ionic liquids is applied to deposition of a nucleotide monomer, oligonucleotide, or polynucleotide to a suitable substrate, especially for the fabrication of polynucleotide arrays. An apparatus as pictured in FIG. 4 may be used to contact the insoluble planar substrate with the nucleotide monomer, oligonucleotide, or polynucleotide dissolved in the solvent comprising an ionic liquid. The apparatus shown in FIG. 4 includes a substrate station 20 on which can be mounted a substrate 14. Substrate station 20 can include a vacuum chuck connected to a suitable vacuum source (not shown) to retain a substrate 14 without exerting too much pressure thereon, since substrate 14 is often made of glass. A dispensing head 210 is retained by a head retainer 208. Head 210 can be positioned to face substrate station 20 by a positioning system. The positioning system includes a carriage 62 connected to substrate station 20, a transporter 60 controlled by a processor 140 through line 66, and a second transporter 100 controlled by processor 140 through line 106. Transporter 60 and carriage 62 are used execute one axis positioning of the station 20 facing the dispensing head 210 by moving station 20 in the direction of arrow 63, while transporter 100 is used to provide two axis adjustment of the position of head 210 in a vertical direction 202 or in the direction 204. Further, once substrate station 20 has been positioned facing head 210, the positioning system will be used to scan head 208 across a mounted substrate 14, typically line by line (although other scanning configurations could be used). However, it will be appreciated that both transporters 60 and 100, or either one of them, with suitable construction, can be used to perform any necessary positioning (including the foregoing scanning) of head 210 with respect to any of the stations. Thus, when the present application recites "positioning" one element (such as head 210) in relation to another element (such as station 20) it will be understood that any required moving can be accomplished by moving either element or a combination of both of them.

Figure 4:
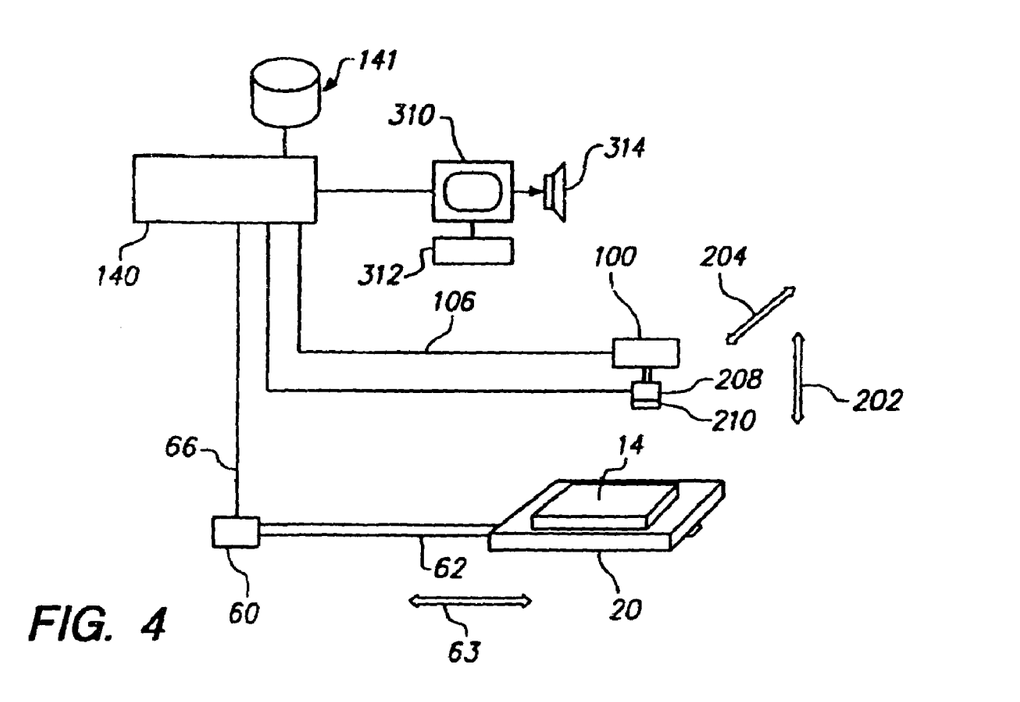
FIG. 4 shows components of an apparatus useful in fabricating polynucleotide arrays according to the present invention.

The apparatus further includes a display 310, speaker 314, and operator input device 312. Operator input device 312 may, for example, be a keyboard, mouse, or the like. Processor 140 has access to a memory 141, and controls head 210 (and activation of the ejectors therein), operation of the positioning system, operation of each jet in print head 210, display 310 and speaker 314. Memory 141 may be any suitable device in which processor 140 can store and retrieve data, such as magnetic, optical, or solid state storage devices (including magnetic or optical disks or tape or RAM, or any other suitable device). Any processor described herein may include a general purpose digital microprocessor (such as typically used in a programmable computer) suitably programmed to execute all of the steps required by it, or any hardware or software combination which will perform the required functions.

Head 210 may be of a type commonly used in an ink jet type of printer and may, for example, have multiple drop dispensing orifices communicating with one or more chambers for holding either previously obtained polynucleotide solution (deposition method), or a solution of a polynucleotide monomer (for in situ synthesis of polynucleotides on the surface of the substrate 14). Ejectors are positioned in the one or more chambers, each opposite a corresponding orifice. For example, each ejector may be in the form of an electrical resistor operating as a heating element under control of processor 140 (although piezoelectric elements could be used instead). Each orifice with its associated ejector and portion of the chamber, defines a corresponding pulse jet. In this manner, application of a single electric pulse to an ejector causes a droplet to be dispensed from a corresponding orifice. Certain elements of the head 210 can be adapted from parts of a commercially available thermal inkjet print head device available from Hewlett-Packard Co. as part no. HP51645A. One suitable head configuration is described in more detail in U.S. patent application entitled "A Multiple Reservoir Ink Jet Device for the Fabrication of Biomolecular Arrays" by Caren et al., Ser. No. 09/150,507 filed Sep. 9, 1998, now U.S. Pat. No. 6,461,812. Modifications to the above apparatus which may be made depending on the array formation method are described in co-pending U.S. patent applications entitled "Fabricating Biopolymer Arrays" by Webb et al., Ser. No. 09/302,922 filed Apr. 30, 1999, now U.S. Pat. No. 6,323,043, and U.S. Patent No. 6,242,266 to Schleifer et al.

Following contact of the substrate with the ionic liquid solution for a period of time and under conditions sufficient for the nucleotide monomer, oligonucleotide, or polynucleotide to become immobilized on the substrate surface, as described above, the surface of the resultant array may be further processed as desired in order to prepare the array for use. For example, further iterations of the synthesis cycle may be performed for in situ synthesis. As another example, the array surface may be washed to removed unbound reagent, e.g. unreacted polymer, and the like. Any convenient wash solution and protocol may be employed, e.g. flowing an aqueous wash solution, e.g. water, methanol, acetonitrile, and the like, across the surface of the array, etc. The surface may also be dried and stored for subsequent use, etc.

The apparatus of FIG. 4 is useful for the practice of the invention, but is not required, as a number of other known methods are available and may be used for contacting the substrate with the nucleotide monomer, oligonucleotide, or polynucleotide dissolved in the solvent comprising an ionic liquid. Modifications of these known methods within the capabilities of a skilled practitioner in the art as well as other methods known to those of skill in the art may be employed. For example, U.S. Pat. No. 6,110,426 to Shalon, et al. describes a method of dispensing a known volume of a reagent at each selected array position, by tapping a capillary dispenser on the substrate under conditions effective to draw a defined volume of liquid onto the substrate. Another method employs uses an array of pins dipped into corresponding wells, e.g., the 96 wells of a microtitre plate, for transferring an array of samples to a substrate, such as a porous membrane. One such array of pins is designed to spot a membrane in a staggered fashion, for creating an array of 9216 spots in a 22 by 22 cm area (Lehrach, et al., "Hybrididization Fingerprinting in Genome Mapping and Sequencing," in Genome Analysis, Vol. 1 (1990, Davies and Tilgham, Eds., Cold Spring Harbor Press), 39-81). A different method has been described which uses a vacuum manifold to transfer a plurality, e.g., 96, of aqueous samples of DNA from 3 millimeter diameter wells to a porous membrane for making ordered arrays of DNA on a porous membrane, i.e. a "dot blot" approach. A common variant of this procedure is a "slot-blot" method in which the wells have highly-elongated oval shapes. Khrapko, et al. (DNA Sequence 1:375-388 (1991)) describes a method of making an oligonucleotide matrix by spotting DNA onto a thin layer of polyacrylamide. The spotting is done manually with a micropipette. Another alternate method of creating ordered arrays of nucleic acid sequences involving synthesizing different nucleic acid sequences at different discrete regions of a substrate has been described. See Fodor et al., Science 251:767-773 (1991). A related method has been described by Southern, et al. Genomics 13:1008-1017 (1992). See also U.S. Pat. No. 5,143,854 to Pirrung et al., and PCT patent publications WO 90/15070 and 92/10092 for further methods for making arrays of oligonucleotide probes by depositing solutions of reagents on a substrate surface.

Still other methods and apparatus for fabrication of polynucleotide arrays are described in, e.g. U.S. Pat. No. 6,242,266 to Schleiffer et al., which describes a fluid dispensing head for dispensing droplets onto a substrate, and methods of positioning the head in relation to the substrate. U.S. Pat. No. 6,180,351 to Cattell and U.S. Pat. No. 6,171,797 to Perbost describe additional methods useful for fabricating polynucleotide arrays. Methods for fabrication of arrays may include, for example, using a pulse jet such as an inkjet type head to deposit a droplet of reagent solution for each feature. Such a technique has been described, for example, in PCT publications WO 95/25116 and WO 98/41531, and elsewhere. In such methods, the head has at least one jet which can dispense droplets of a fluid onto a substrate, the jet including a chamber with an orifice, and including an ejector which, when activated, causes a droplet to be ejected from the orifice. The head may particularly be of a type commonly used in inkjet printers, in which a plurality of pulse jets (such as those with thermal or piezoelectric ejectors) are used, with their orifices on a common front surface of the head. The head is positioned with the orifice facing the substrate. Multiple fluid droplets (where the fluid comprises the nucleotide monomer, oligonucleotide, or polynucleotide dissolved in the solvent comprising an ionic liquid) are dispensed from the head orifice so as to form an array of droplets on the substrate (this formed array may or may not be the same as the final desired array since, for example, multiple heads can be used to form the final array and multiple passes of the head(s) may be required to complete the array).

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

It should be specifically understood though, that the present invention is not limited to pulse jet type deposition systems. In particular, any type of array fabricating apparatus can be used to contact the substrate with the ionic liquid solution, including those such as described in U.S. Pat. No. 5,807,522, or apparatus which may employ photolithographic techniques for forming arrays of moieties, such as described in U.S. Pat. No. 5,143,854 and U.S. Pat. No. 5,405,783, or any other suitable apparatus which can be used for fabricating arrays of moieties. For example, robotic devices for precisely depositing aqueous volumes onto discrete locations of a support surface, i.e. arrayers, are also commercially available from a number of vendors, including: Genetic Microsystems; Cartesian Technologies; Beecher Instruments; Genomic Solutions; and BioRobotics. Other methods and apparatus are described in U.S. Pat. Nos. 4,877,745; 5,338,688; 5,474,796; 5,449,754; 5,658,802; and 5,700,637. Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505, WO 97/14706, WO 98/30575; EP 742 287; and EP 799 897. See also Beier et al. "Versatile derivatisation of solid support media for covalent bonding on DNA-microchips", Nucleic Acids Research (1999) 27: 1970-1977.

In general, the product of the coupling reaction when performed in the 5' to 3' direction, when performed in a solid phase system upon an insoluble planar substrate, may be represented by the following structural formula:

(III)

Wherein:

○ represents the insoluble planar substrate or an oligonucleotide chain bound to the insoluble planar substrate;

A represents H or an optionally protected hydroxyl group;

B is a purine or pyrimidine base whose exocyclic amine functional group is optionally protected; and R is a suitable protecting group, "Y" is hydrido or hydrocarbyl, typically alkyl, alkenyl, aryl, aralkyl, or cycloalkyl. Preferably, Y represents: lower alkyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Most preferably, Y represents methyl, β-cyanoethyl, or 4-nitrophenylethyl.

The synthetic methods of the invention may be conducted on any substrate having a surface to which chemical entities may bind. Preferred substrate materials provide physical support for the deposited material and endure the conditions of the deposition process and of any subsequent treatment or handling or processing that may be encountered in the use of the particular array. Suitable substrates may have a variety of forms and compositions and may derive from naturally occurring materials, naturally occurring materials that have been synthetically modified, or synthetic materials. Examples of suitable support materials include, but are not limited to, nitrocellulose, glasses, silicas, teflons, and metals (for example, gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

Prior to being contacted with the solution containing the ionic liquid and the nucleotide monomer, oligonucleotide, or polynucleotide, the insoluble substrate has a surface reactive group which, when contacted with the solution, reacts to covalently bind the nucleotide monomer, oligonucleotide, or polynucleotide to the substrate. The surface reactive group may vary in different embodiments of the invention. In one embodiment, the surface reactive group is part of the composition of the planar substrate base material. In another embodiment, modifications to the surface of the base material may present a different surface reactive group than possible from the base material itself. Such modifications may include one or more different layers of compounds that serve to modify the properties of the surface in a desirable manner. Such modification layers include, but are not limited to, inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric. Modifications of insoluble substrate materials may or may not have separate functional moieties attached thereto.

The substrate may be functionalized to form a "linking moiety" having a surface reactive group to bond to the first deposited monomer. Suitable techniques for functionalizing substrates with such linking moieties are described, for example, in Southern, E. M., Maskos, U. and Elder, J. K., Genomics, 13: 1007-1017, 1992. The initial monomer of the oligonucleotide to be synthesized on the substrate surface is typically bound to a linking moiety which is in turn bound to a surface hydrophilic group, e.g., to a surface hydroxyl moiety present on a silica substrate. Methods similar to those disclosed in, e.g. U.S. Pat. No. 5,688,642 to Chrisey et al., may be used. The Chrisey et al. '642 patent describes coating a substrate with molecules, such as aminosilanes, whose reactivity with nucleic acid molecules can be transformed by irradiation; this patent also teaches the use of a heterobifunctional crosslinker to promote covalent binding of the nucleic acid oligomers to the coating molecules. In yet another embodiment of the current invention, the surface reactive group may be located upon a nucleoside moiety immobilized upon the substrate base material (e.g. via a direct bond to the base material or via a surface modification of the base material). The nucleoside moiety may be a portion of an immobilized nucleotide monomer, a portion of an immobilized oligonucleotide, or a portion of an immobilized polynucleotide. The surface reactive group may include a hydroxyl group, e.g. a 3' or 5' hydroxyl group of a terminal nucleoside moiety of an immobilized nucleoside, immobilized oligonucleotide, or immobilized polynucleotide.

In array fabrication, the quantities of polynucleotide available are usually very small and expensive. Additionally, sample quantities available for testing are usually also very small and it is therefore desirable to simultaneously test the same sample against a large number of different probes on an array. Therefore, one embodiment of the invention provides for fabrication of arrays with large numbers of very small, closely spaced features Arrays may be fabricated with features that may have widths (that is, diameter, for a round spot) in the range from a minimum of about 10 micrometers to a maximum of about 1.0 cm. In embodiments where very small spot sizes or feature sizes are desired, material can be deposited according to the invention in small spots whose width is in the range about 1.0 micrometer to 1.0 mm, usually about 5.0 micrometers to 0.5 mm, and more usually about 10 micrometers to 200 micrometers. Interfeature areas will typically (but not essentially) be present which do not carry any polynucleotide. It will be appreciated though, that the interfeature areas could be of various sizes and configurations.

Figure 2:
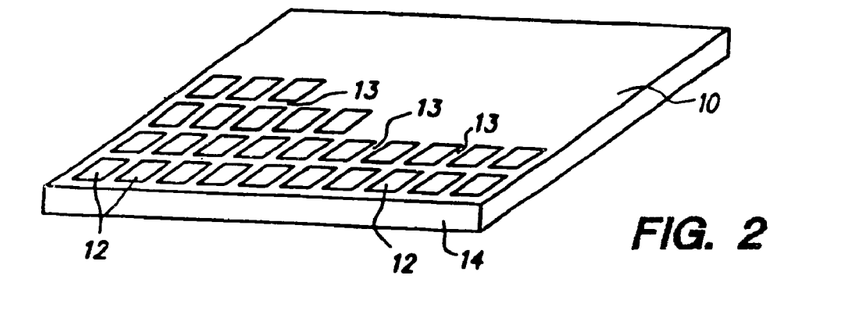
FIG. 2 depicts a substrate bearing multiple arrays, as may be produced as described herein.
Figure 3:
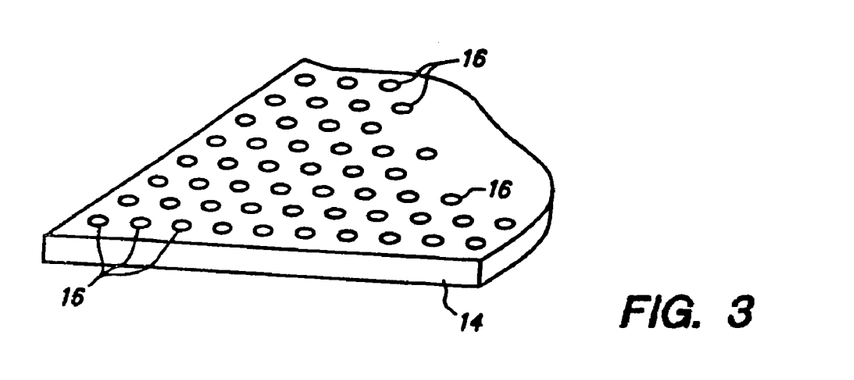
FIG. 3 is an enlarged view of a portion of FIG. 2 showing some of the identifiable individual regions (spots, or features) of a single array of FIG. 2.

Referring now to FIGS. 2 and 3, the invention as described herein may be practiced to produce one or more arrays 12 (only some of which are shown in FIG. 2) across the surface of a single substrate 14. The arrays 12 produced on a given substrate need not be identical and some or all could be different. FIG. 3 depicts a single array 12 having multiple spots or features, 16. An array 12 may contain any number of features, generally including at least tens of features, usually at least hundreds, more usually thousands, and as many as a hundred thousand or more features. All of the features 16 may be different, or some or all could be the same. Each feature 16 carries a predetermined moiety or a predetermined mixture of moieties, such as a particular polynucleotide sequence or a predetermined mixture of polynucleotides. The features of the array may be arranged in any desired pattern, e.g. organized rows and columns of features (for example, a grid of features across the substrate surface), a series of curvilinear rows across the substrate surface (for example, a series of concentric circles or semi-circles of features), and the like. In embodiments where very small feature sizes are desired, the density of features on the substrate may range from at least about ten features per square centimeter, or preferably at least about 35 features per square centimeter, or more preferably at least about 100 features per square centimeter, and up to about 1000 features per square centimeter, or preferably up to about 10,000 features per square centimeter, or more preferably up to 100,000 features per square centimeter. Each feature carries a predetermined polynucleotide (which includes the possibility of mixtures of polynucleotides).

In one embodiment, about 10 to 100 of such arrays can be fabricated on a single substrate (such as glass). In such embodiment, after the substrate has the polynucleotides on its surface, the substrate may be cut into substrate segments, each of which may carry one or two arrays. It will also be appreciated that there need not be any space separating arrays from one another. Where a pattern of arrays is desired, any of a variety of geometries may be constructed, including for example, organized rows and columns of arrays (for example, a grid of arrays, across the substrate surface), a series of curvilinear rows across the substrate surface (for example, a series of concentric circles or semi-circles of arrays), and the like.

The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 300 mm, usually about 4 mm to 150 mm, more usually about 4 mm to 125 mm; a width in the range about 4 mm to 300 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The substrate surface onto which the polynucleotides are bound may be smooth or substantially planar, or have irregularities, such as depressions or elevations. The configuration of the array may be selected according to manufacturing, handling, and use considerations.

Ionic liquids that may be used include organic salts that are fluid below about 80° C. at around normal atmospheric pressure (about 1 atmosphere at sea level). The organic salts generally have an organic cation and either an inorganic or organic counterion. The organic cation is preferably an N-substituted pyridine having the following structure:

(IV)

wherein R is alkyl and each R' is independently selected from hyrido, alkyl, or halogen;

or a 1,3 di-substituted imidazole having the following structure:

(V)

wherein each R is independently selected from alkyl, each R' is independently selected from hydrido, alkyl, or halogen, and R" is selected from hydrido or methyl.

Preferred organic cations include 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium, N-ethylpyridinium, N-butylpyridinium, N-hexylpyridinium, 4-methyl-N-butyl-pyridinium, 3-methyl-N-butyl-pyridinium, 4-methyl-N-hexyl-pyridinium, 3-methyl-N-hexyl-pyridinium, 4-methyl-N-octyl-pyridinium, 3-methyl-N-octyl-pyridinium, 3,4-dimethyl-N-butyl-pyridinium, and 3,5-dimethyl-N-butyl-pyridinium.

Preferred anions of the ionic liquid are chloride ($Cl^-$), bromide ($Br^-$), tetrafluoroborate ($[BF_4]^-$), hexafluorophosphate ($[PF_6]^-$), $[SbF_6]^-$, $[CuCl_2]^-$, $[AlCl_4]^-$, $[Al_2Cl_7]^-$, $[Al_3Cl_{10}]^-$, methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), bis(trifluoromethylsulfonyl)imide (($CF_3SO_2)_2N^-$), bis(perfluoroethylsulfonyl)imide (($C_2F_5SO_2)_2N^-$), and tris(trifluoromethylsulfonyl)methide (($CF_3SO_2)_3C^-$). Ionic liquids are available from Covalent Associates (Woburn, Mass.), Aldrich Chemical Company Milwaukee, Wis.), Solvent Innovation (Köln, Germany), and Acros Organics (Geel, Belgium).

In one embodiment, to perform the coupling reaction, a nucleotide monomer, oligonucleotide, or polynucleotide is dissolved in a solution having at least 98 percent by weight of ionic liquid, whereupon an insoluble substrate, preferably a planar substrate, is contacted with the solution containing ionic liquid and the nucleotide monomer, oligonucleotide, or polynucleotide. In other embodiments, the solution has at least about 90% ionic liquid, or at least about 75% ionic liquid, or at least about 50% ionic liquid, or at least about 25% ionic liquid, or at least about 10% ionic liquid. Co-solvents that may be mixed into the ionic liquid include but are not limited to acetonitrile, tetrahydrofuran, dimethylformamide, methylene chloride, propylene carbonate, adiponitrile, toluene, dioxane, dimethylsulfoxide, and N-methyl pyrrolidone. In another embodiment, the nucleotide monomer, oligonucleotide, or polynucleotide is dissolved in a solvent that is 100 percent by weight ionic liquid. An activator compound is typically included in a concentration of about 0.05 molar up to about 0.5 molar. The activator is generally tetrazole, S-ethyl-thiotetrazole, 4-nitrotriazole, or dicyanoimidazole, although other acidic azoles may be used. One potential advantage of using an ionic liquid is that the ionic liquid may serve as the activator.

In one embodiment of the invention, a monomer nucleoside phosphoramidite is dissolved in the solvent comprising the ionic liquid, and the resulting solution is deposited upon the surface of the planar substrate, and the process is repeated multiple times, analogous to conventional polynucleotide synthesis. The invention also encompasses the formation of an internucleotide bond between two polynucleotides or oligonucleotides, or between a polynucleotide and an oligonucleotide, resulting in an extended polynucleotide immobilized on the array surface. In such case, one of the polynucleotides or oligonucleotides is dissolved in the solvent comprising the ionic liquid, and the substrate to be contacted with the solution bears the other polynucieotide or oligonucleotide. The skilled practitioner in the art will realize that one of the nucleoside moieties must be activated, as in a phosphoramidite. Such modification is well known in the art. The invention also encompasses embodiments where the oligonucleotide or polynucleotide dissolved in the solvent comprise modified oligonucleotides or modified polynucleotides, especially where the modified oligo- or -polynucleotides are "activated", or more susceptible to bond formation. Such modification of the oligo- or poly-nucleotides may be accomplished using known chemistries previously used for immobilizing oligo- or polynucleotides to insoluble substrates. Examples of such modifications may be found in: *Polymer-supported Reactions in Organic Chemistry*, Hodge, P. & Sherrington, D. C., (John Wiley & Sons, New York, N.Y. 1980); *Advanced Organic Chemistry of Nucleic Acids*, Shabarova, Z. & Bogdanov, A., (VCH, Weinheim, Germany 1994), pages 531-545.

In the case of array fabrication, different nucleotide monomers and activator may be deposited at different addresses on the substrate during any one cycle so that the different features of the completed array will have polynucleotides with different sequences. One or more intermediate further steps may be required in each cycle, such as the conventional oxidation, capping and washing steps in the case of in situ fabrication of polynucleotide arrays (these steps may be performed by flooding the array surface with the appropriate reagents).

In certain embodiments of the invention, the probes are arranged on the substrate either by immobilization, e.g. by covalent attachment, of a pre-synthesized probe, or by synthesis of the probe on the substrate (in situ synthesis). In fabricating a polynucleotide array, typically each region on the substrate surface on which an array will be or has been formed ("array regions") is completely exposed to one or more reagents. For example, the array regions will often be exposed to one or more reagents to form a suitable layer on the surface which binds to both the substrate and the polynucleotide. In in situ synthesis the array regions will also typically be exposed to the oxidizing, deblocking, and optional capping reagents. Similarly, particularly in fabrication by depositing previously obtained oligonucleotides or polynucleotides, it may be desirable to expose the array regions to a suitable blocking reagent to block locations on the surface at which there are no features from non-specifically binding to target.

In the conventional synthesis method depicted schematically in FIG. 1, it is typical to use an aqueous solution of iodine for the oxidation step. However, phosphoramidite reagents that have been activated for coupling are highly reactive with water. The invention may be extended to include using ionic liquids as solvents elsewhere in the synthesis cycle to reduce or substantially eliminate the presence of water during oxidation and deprotection. Thus, for example, in polynucleotide array synthesis, the current invention may allow the number of wash steps (with non-aqueous solvent) over all of the addresses on the surface of the array to be reduced, with potential concomitant savings in time and solvents.

The method of the invention lends itself to synthesis of polynucleotides on array substrates in either the 3'-to-5' or the 5'-to-3' direction. In the latter case, the initial step of the synthetic process involves attachment of an initial nucleoside to the array substrate at the 5' position, leaving the 3' position available for covalent binding of a subsequent monomer. The coupling reaction in which the nucleoside monomer becomes covalently attached to the 3' hydroxyl moiety of the substrate bound nucleoside is conducted under reaction conditions essentially identical to those described for the 3'-to-5' synthesis. The synthesis cycle is then continued with the (optional) capping step, the oxidation of the internucleotide bond, and the deprotection of the active site hydroxyl in preparation for the next synthesis cycle, which is repeated until a polynucleotide having the desired sequence and length is obtained. The synthesis is repeated at each address of the array to build up the desired sequence polynucleotide at each address of the array. Following synthesis, the polynucleotide may, if desired, be cleaved from the solid support. The details of the synthesis in either the 3'-to-5' or the 5'-to-3' direction will be readily apparent to the skilled practitioner based on the prior art and the disclosure contained herein.

In particular embodiments, the reaction is geared to producing planar substrates having immobilized thereupon "native" polynucleotides, i.e. substantially identical to those that might be isolated from nature. In other embodiments, polynucleotide analogues may be immobilized upon the planar substrate, where the polynucleotide analogues may have 'modified' (not occurring in nature) phosphodiester backbones or modified bases attached to the sugar groups in the phosphodiester backbones. In another embodiment, after the dissolved nucleotide monomer, oligonucleotide, or polynucleotide has been immobilized to the planar substrate, it is modified, e.g. by oxidation, to form the ultimate polynucleotide product. The present invention encompasses materials and methods for use in fabricating insoluble substrates having immobilized thereupon polynucleotides, polynucleotide intermediates, and/or polynucleotide analogues. The invention also encompasses reagents and methods allowing the immobilization of the polynucleotides/intermediates/analogues to be conducted under a wide range of conditions and allowing for the use of a variety of protecting groups. This wide range includes the use of solvents comprising one or more ionic liquids and, optionally, one or more co-solvents.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method of immobilizing a nucleotide monomer, oligonucleotide, or polynucleotide upon an insoluble substrate, the method comprising
   a) dissolving a nucleotide monomer, oligonucleotide, or polynucleotide in a solvent comprising an ionic liquid such that the resulting solution comprises at least 50% by weight ionic liquid, and
   b) contacting the insoluble substrate with the solution resulting from a) under conditions and for a time sufficient to immobilize the nucleotide monomer, oligonucleotide, or polynucleotide upon the insoluble substrate.

2. The method of claim 1 wherein the solution includes at least about 75% by weight of an ionic liquid.

3. The method of claim 1 wherein the solution includes at least about 90% by weight of an ionic liquid.

4. The method of claim 1 wherein the solution includes at least about 98% by weight of an ionic liquid.

5. The method of claim 1 wherein the ionic liquid is an organic salt comprising a substituted heterocyclic organic cation.

6. The method of claim 5 wherein the ionic liquid is an organic salt comprising a cation selected from an N-substituted pyridine and a 1,3-disubstituted imidazole.

7. The method of claim 5 wherein the organic salt comprises an anion selected from chloride ($Cl^-$), bromide ($Br^-$), tetrafluoroborate ($[BF_4]^-$), hexafluorophosphate ($[PF_6]^-$), $[SbF_6]^-$, $[CuCl_2]^-$, $[AlCl_4]^-$, $[Al_2Cl_7]^-$, $[Al_3Cl_{10}]^-$, methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), bis(trifluoromethylsulfonyl)imide (($CF_3SO_2)_2N^-$), bis(perfluoroethylsulfonyl)imide (($C_2F_5SO_2)_2N^-$), and tris(trifluoromethylsulfonyl)methide (($CF_3SO_2)_3C^-$).

8. The method of claim 5 wherein the organic salt is characterized as being a liquid when being >98% pure and at standard temperature and pressure.

9. The method of claim 5 wherein the organic salt is characterized as being a liquid below about 80° C. at about standard atmospheric pressure.

10. The method of claim 5 wherein the cation is an N-substituted pyridine having the formula wherein R is alkyl and each R' is independently selected from hyrido, alkyl, or halogen group.

11. The method of claim 5 wherein the cation has the formula wherein each R is independently selected from alkyl, each R' is independently selected from hydrido, alkyl, or halogen, and R" is selected from hydrido or methyl.

12. The method of claim 1 further comprising conducting steps a) and b) at each of a plurality of sites on the insoluble substrate to form an addressable array of polynucleotides on the insoluble substrate.

13. The method of claim 1 wherein the contacting is performed by depositing droplets of the solution resulting from a) on the substrate using an ink jet device.

14. A method of forming a bond between a reactive group immobilized on an insoluble substrate and a molecule selected from the group consisting of a nucleotide monomer, an olignucleotide, and a polynucleotide; the method comprising contacting the reactive group with a solution comprising the molecule and at least 50% by weight of an ionic liquid ionic liquid.

15. The method of claim 14 wherein the solution includes at least about 75% by weight of an ionic liquid.

16. The method of claim 14 wherein the solution includes at least about 90% by weight of an ionic liquid.

17. The method of claim 14 wherein the solution includes at least about 98% by weight of an ionic liquid.

18. The method of claim 14 wherein the bond is an internucleotide bond.

19. The method of claim 18, further comprising contacting the internucleotide bond with an oxidizing reagent to oxidize the internucleotide bond.

20. The method of claim 19 wherein the insoluble substrate is a planar substrate having a surface, an array of polynucleotides being arranged upon the surface.

21. The method of claim 14 wherein the ionic liquid is an organic salt comprising a substituted heterocyclic organic cation.

22. The method of claim 14 wherein the ionic liquid is an organic salt comprising a cation selected from an N-substituted pyridine and a 1,3-disubstituted imidazole.

23. The method of claim 21, the organic salt comprising an anion selected from chloride (Cl$^-$), bromide (Br$^-$), tetrafluoroborate ([BF$_4$]$^-$), hexafluorophosphate ([PF$_6$]$^-$), [SbF$_6$]$^-$, [CuCl$_2$]$^-$, [AlCl$_4$]$^-$, [Al$_2$Cl$_7$]$^-$, [Al$_3$Cl$_{10}$]$^-$, methylsulfate (CH$_3$SO$_4^-$), trifluoroacetate (CF$_3$CO$_2^-$), heptafluorobutanoate (CF$_3$(CF$_2$)$_2$CO$_2^-$), triflate (CF$_3$SO$_2^-$), nonaflate (C$_2$F$_5$SO$_2^-$), bis(trifluoromethylsulfonyl)imide ((CF$_3$SO$_2$)$_2$N$^-$), bis(perfluoroethylsulfonyl)imide ((C$_2$F$_5$SO$_2$)$_2$N$^-$), and tris(trifluoromethylsulfonyl)methide ((CF$_3$SO$_2$)$_3$C$^-$).

24. The method of claim 14, the organic salt having the characteristic of being a liquid when being >98% pure and at standard temperature and pressure.

25. The method of claim 21 wherein the cation is an N-substituted pyridine having the formula wherein R is alkyl and each R' is independently selected from hyrido, alkyl or halogen group.

26. The method of claim 21 wherein the cation has the formula wherein each R is independently selected from alkyl, each R' is independently selected from hydrido, alkyl, or halogen, and R" is selected from hydrido or methyl.

27. The method of claim 14 wherein the contacting is performed by depositing droplets of the solution on the substrate using an ink jet device.

28. The method of claim 14 wherein the organic salt is characterized as being a liquid below about 80° C. at about standard atmospheric pressure.

* * * * *